United States Patent [19]

O'Neill et al.

[11] Patent Number: 5,300,481
[45] Date of Patent: Apr. 5, 1994

[54] METHODS FOR CONTROLLING FLOWERING IN PLANTS

[75] Inventors: Sharman D. O'Neill; David L. Van Tassel, both of Davis, Calif.

[73] Assignee: The Regents of the University of California, Oakland, Calif.

[21] Appl. No.: 58,735

[22] Filed: May 5, 1993

[51] Int. Cl.$^5$ .............................................. A01N 43/38
[52] U.S. Cl. .................................................... 504/284
[58] Field of Search ......................................... 504/284

[56] References Cited

U.S. PATENT DOCUMENTS 3,923,492 12/1975 Collins et al. ........................ 504/284
4,614,807 9/1986 Flaugh ................................. 548/507

FOREIGN PATENT DOCUMENTS

WO89/01472 2/1989 PCT Int'l Appl. .

OTHER PUBLICATIONS

Reiter, R. J., "Pineal Melatonin: Cell Biology of Its Synthesis and of Its Physiological Interactions," *Endocrine Reviews*, 12(2):151–180 (May, 1991).

O'Neill, S. D., "The Photoperiodic Control of Flowering: Progress toward Understanding the Mechanism of Induction," *Photochemistry and Photobiology*, 56(5):789–801 (1992).

Utiger, R. D., "Melatonin—The Hormone of Darkness," *New England J. Med.*, 327(19):1377–1379 (Nov. 5, 1992).

Pöggeler, B., et al., "Pineal Hormone Melatonin Oscillates Also in the Dinoflagellate Gonyaulax polyedra," *Naturwissenschaften*, 78:268–269 (1991).

*Primary Examiner*—Richard L. Raymond
*Assistant Examiner*—Brian Bembenick
*Attorney, Agent, or Firm*—Townsend and Townsend Khourie and Crew

[57] ABSTRACT

This invention is the exogenous application of serotonin, melatonin and related derivatives to regulate flowering in plants.

28 Claims, 2 Drawing Sheets

METHODS FOR CONTROLLING FLOWERING IN PLANTS

BACKGROUND OF THE INVENTION

Field of the Invention

This invention is the exogenous application of serotonin, melatonin and related derivatives to regulate flowering in plants. Flowering involves the developmental transition of the shoot meristem from vegetative to reproductive growth. In the majority of species of flowering plants, which includes nearly all crop plants and horticultural species, the transition to flowering is regulated by daylength, and thus these species are considered to be "photoperiodic" with regard to their reproductive regulation. This limits year-round production of many crops, and breeding efforts to modify photoperiodic behavior have been critical to development of early season varieties in crops such as strawberry.

Melatonin is known to be a potent hormone associated with photoperiodic reproductive behavior in animals, lower organisms and dinoflagellates and its cell and molecular biology has been extensively investigated in animal systems. However, melatonin has not been previously reported in plants. This invention is based on the discovery that melatonin induces flowering in plants. The metabolic pathway for production of melatonin uses serotonin as a precursor (see FIG. 1). The relative amounts of serotonin to melatonin are responsible for triggering flowering. Exogenous levels of serotonin are able to inhibit flowering.

Regulation of flowering is of significant economic value. The inhibition of premature flowering and stimulation of flowering after a plant reaches maximal size can increase flower and seed yields dramatically. Alternatively, in geographical regions where the growing season is short, the stimulation of precocious flowering can increase the range of late-maturing crops, for example soybean. Finally, by stimulating flowering to be uniform among a field or stand, harvest costs can be minimized.

SUMMARY OF THE INVENTION

This invention provides for a method for regulating the flowering of a plant by applying a compound of the formula I in an amount sufficient to induce flowering

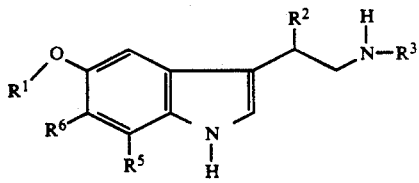

wherein $R^1$ is selected from the group consisting of hydrogen and lower alkyl of 1 to 4 carbon atoms; $R^2$ is selected from the group consisting of hydrogen and alkyl of 1 to 4 carbon atoms; $R^3$ is selected from the group consisting of hydrogen and —$COR^4$ wherein $R^4$ is a alkyl of 1 to 4 carbon atoms; and $R^5$ and $R^6$ are independently selected from the group consisting of hydrogen, chloro, fluoro, bromo and iodo. Preferred compounds have substituents as follows: $R^1$ is a methyl, $R^2$ is hydrogen, $R^3$ is hydrogen, and $R^5$ and $R^6$ are hydrogen. Also preferred are compounds wherein $R^1$ is a methyl or ethyl, $R^2$ is hydrogen, $R^3$ is $COR^4$ where $R^4$ is methyl, and $R^5$ and $R^6$ are hydrogen. Preferred compounds are 5-methoxy N-acetyltryptamine, and 5-methoxytryptamine. The target plants can be either monocot or dicot. Photoperiodic plants are preferred especially short-day plants.

The invention further provides for aqueous solutions for spraying the active compounds upon the foliage of plants. A preferred foliar formulation suitable for dilution with water comprising a surfactant and a composition of the formula of claim 1 wherein the surfactant is selected from the group consisting of polyoxyethylenesorbitan (monolaurate) (Tween ® and α-[4-(1,1,3,3,-Tetramethylbutyl)phenyl]-ω-hydrosypoly(oxy-1,2-ethanediyl) where the number of ethoxy groups average 10, sold as Triton ® X-100 (Rohm and Haas). The preferred rates of application for the active compound being at a concentration of 0.5 ppm to 1000 ppm more preferred between about 10 ppm to about 100 ppm. In rates per hectare, a useful range is at a rate of 1 to 20 kg active compound per hectare. The plants preferably have at least one fully expanded leaf. The aqueous solutions comprise active ingredients as set forth above.

This invention also provides for a method for regulating the flowering a plant by applying a compound selected from the group consisting of serotonin and N-acetylserotonin in an amount sufficient to control flowering. The preferred plants, methods of application and rates of application are as provided above.

DEFINITIONS

The following definitions refer to the various terms used throughout the disclosure.

The term "halo" refers to fluoro, chloro, bromo, and iodo.

The term "alkyl of 1 to 4 carbon atoms" refers to the straight and branched aliphatic radicals of 1-n carbon atoms including methyl, ethyl, propyl, isopropyl, n-butyl, isobutyl, sec-butyl, and tert-butyl and the like.

Any limits in number are meant to be inclusive.

DETAILED DESCRIPTION

Figure 1:
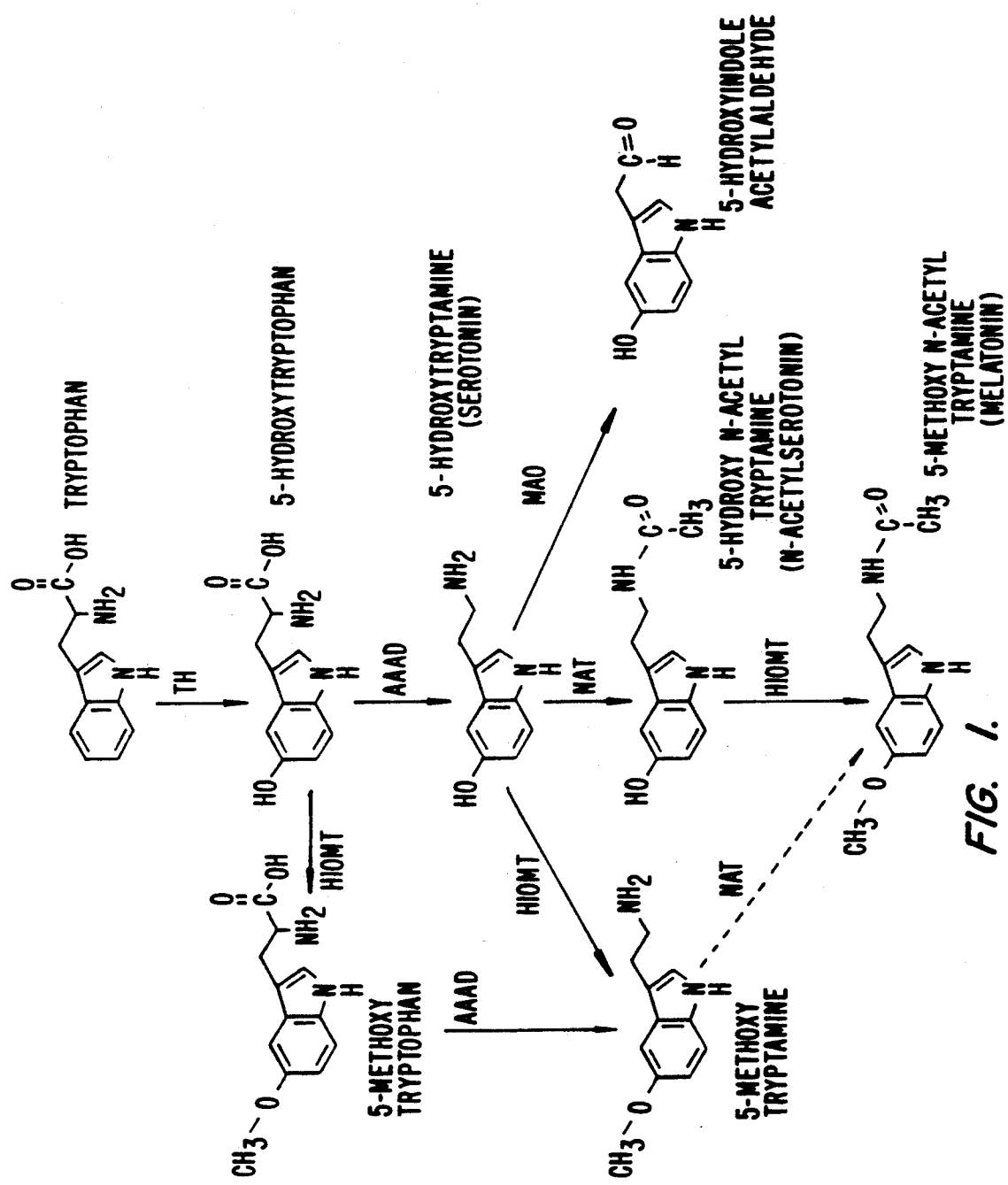
FIG. 1 is schematic depiction of the reactions leading to melatonin.

A. Chemical Synthesis of Serotonin, Melatonin and its Related Indole Analogs The compounds of this invention may be prepared according to any of several processes employing common reactants and procedures. Methods for preparing the melatonin analogs used in the present invention can be found in U.S. Pat. No. 4,614,807, and European Patent Application Publication No. 281,242, both incorporated herein by reference.

Briefly, the preparation of known 6-halo or 7-halomelatonins and related N-acyl derivatives may be synthesized as follows. Phenol or the halogenated derivatives thereof are nitrated para to the hydroxy group to yield the 4-nitrophenol. Alkylation of the hydroxy moiety produces the corresponding alkoxy(halo)nitrobenzenes. Reduction of the nitro group followed by oxidation to a diazonium moiety can be carried out by standard procedures. Reaction of the resultant diazonium salt with 3-acetyl 2-piperidone provides a substituted phenyl hydrazone which can be heated with formic acid to yield 1-oxo-6-alkoxy-7 and/or 8-halo-1,2,3,4-tetrahydro-9H-pyrido[3,4-b]indole. Subsequent treatment with base provides the desired substituted indole-2-carboxylic acids. Decarboxylation by heating in the presence of acid yields the corresponding 5-alkoxy-6 and/or 7-halotryptamine. The primary amine of this compound (where $R_3$ is H) can be acylated by standard means to yield the halomelatonin analogs where $R_4$ is a $C_1$–$C_4$ alkyl.

Other derivatives can be synthesized in a similar manner utilizing suitable protecting groups which are known to those of skill in the art. In particular, 5-hydroxytryptamine can be synthesized from 4-nitrophenol by first protecting the hydroxy moiety then continuing as described above for reduction of the nitro group. Upon completion of the above steps, the protecting group is removed to provide the desired compound.

Synthesis of beta-alkylmelatonins can be achieved as follows. A 5-alkoxy indole, which may or may not be mono or dihalogenated on the phenol ring is reacted with a $C_1$–$C_4$ alkylaldehyde and Meldrum's acid (2,2-dimethyl-4,6-dioxo-1,3-dioxane) in the presence of proline. The resultant product is decomposed by reaction with copper powder and pyridine in a lower alcohol to yield the corresponding ester of beta-alkyl indole propionic acid. The ester is then reacted with hydrazine to produce a hydrazide which is converted to an azide with nitrous acid. The azide is decomposed under Curtius conditions to yield a lactam (1-oxo-4-alkyl 6-alkoxy-7,8-permissibly mono or di-halogenated-9H-1,2,3,4-tetrahydropyrido[3,4-b]indole). The lactam ring is opened by reaction with a base to yield, 2-alkyl-2-(2-carboxy-3-indolyl)ethylamine. Subsequent decarboxylation yields the desired 2-alkyl-2-(3-indolyl)ethylamine. Acylation with an activated form of a carboxylic acid of the formula $R^4CO_2H$ where $R^4$ is a $C_1$–$C_4$ alkyl will yield the requisite analogs of beta-alkylmelatonins which, depending on the starting compound, may or may not be halogenated.

B. Methods for Applying Serotonin, Melatonin and Related Analogs to Plants

This invention finds particular value in its ability to manipulate flowering in short-day plants. Short-day plants are defined by their ability to be induced to flower by decreasing their exposure to sunlight. This is in contrast to long-day plants and day-neutral plants. Short-day plants include strawberry, rice, chrysanthemums, coffee, alfalfa, beans and corn. A review of the classification of plants according to photoperiodic response can be found in D. Vince-Prue, Photoperiodism in Plants, Chapter 1, 1975 (McGraw Hill).

The compounds of the invention may be applied alone or in mixture with other plant regulators, fertilizers, pesticides or fungicides. The compositions may be applied in a mixture with a carrier or, if necessary, other auxiliary agents to form any one of the standard types of preparations commonly used in agriculture, for example, a dust, granules, grains, a wettable powder, an emulsion, an aqueous solution etc.

Suitable solid carriers are clay, talc, kaolin, bentonite, terra abla, calcium carbonate, diatomaceous earth, silica, synthetic calcium silicate kieselguhr, dolomite, powdered magnesia, Fuller's earth, gypsum and the like. Solid compositions may also be in the form of dispersible powders or grains, comprising, in addition to the active ingredient, a surfactant to facilitate the dispersion of the powder or grains in liquid.

Liquid compositions include solutions, dispersions or emulsions containing the active ingredient together with one or more surface-active agents such as wetting agents, dispersing agents, emulsifying agents, or suspending agents.

Surface-active agents may be of the cationic, anionic, or non-ionic type. Suitable agents of the cationic type include, for example, quaternary ammonium compounds. Suitable agents of the anionic type include, for example, soaps such as Triton ® X-100 and Tween ® 20; salts of aliphatic mono-esters of sulphuric acid, for example sodium lauryl sulphate; and salts of sulphonated aromatic compounds, for example sodium dodecyl-benzenesulphonate, sodium, calcium, and ammonium lignosulphonate, butylnaphthalene sulphonate, and a mixture of the sodium salts of diisopropyl- and triisopropyl-naphthalene-sulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitanmonolaurate; the condensation product of the said partial esters with ethylene oxide; and the lecithins.

Suitable suspending agents are, for example, hydrophilic colloids, for example polyvinylpyrollidone and sodium carboxymethylcellulose, and the vegetable gums, for example gum acacia and gum tragacanth. Preferred detergents are polyoxyethylenesorbitan (monolaurate) which is sold as Tween ® 20 (Sigma Laboratories), and α-[4-(1,1,3,3,-Tetramethylbutyl)-phenyl]-ω-hydroxypoly(oxy-1,2-ethanediyl) where the number of ethoxy groups average 10, sold as Triton ® X-100 (Rohm and Haas).

Aqueous solutions, dispersions or emulsions may be prepared by dissolving the active ingredient in water or an organic solvent which may, if desired, contain one or more wetting, dispersing, or emulsifying agents and then, in the case when organic solvents are used, adding the mixture so obtained to water which may, if desired, likewise contain one or more wetting, dispersing or emulsifying agents. Suitable organic solvents are ethylene dichloride, isopropylalcohol, propylene glycol, diacetone alcohol, toluene, mineral oil, kerosene, methylnapthalene, xylenes and trichloroethylene.

The active ingredients may also be formulated by microencapsulation. Microcapsules containing the desired tryptamine derivative may be prepared by coacervation; or, more preferably, by stirred interfacial polymerisation of (for example) an isocyanate/diamine system. The resulting microcapsules may be used as an aqueous suspension.

The compositions which are to be used in the form of aqueous solutions, dispersions or emulsions are generally supplied in the form of a concentrate containing a high proportion of the active ingredient, and the concentrate is then diluted with water before use. These concentrates are usually required to withstand storage for prolonged periods and after such storage, to be capable of dilution with water in order to form aqueous preparations which remain homogeneous for a sufficient time to enable them to be applied by conventional spray equipment. In general, concentrates may conveniently contain from 10-60 percent by weight of the active ingredient or ingredients. Dilute preparations ready for use may contain varying amounts of the active ingredient or ingredients, depending upon the purpose for which they are to be used, and a dilute preparation containing between 0.01 and 10.0 percent and preferably 0.01 and 1 percent, by weight of active ingredient or ingredients may normally be used.

In carrying out the process of the invention, the amount of compound to be applied to regulate the flowering of plants will depend upon a number of factors, for example the particular formulation selected for use, whether the compound is to be applied for foliage or root uptake, the effect desired, and the identity of the plant species whose growth is to be regulated. However, in general, an application rate of from 1 to 20 kg per hectare is suitable, while from 2 to 5 kg per hectare is preferred for most purposes. In foliar sprays, the compositions of this invention can be applied in a range of 0.5 to 1000 ppm. A preferred range is between 10 to 100 ppm. In all cases routine tests are necessary to determine the best rate of application of a specific formulation for any specific purpose for which it is suitable. The optimal time of application would be at dawn when there is low light, high moisture and open stomates. Low light is desirable because melatonin is a light sensitive compound. High moisture and open stomates facilitate absorption of the active compounds by the plants.

Induction of flowering is optimally obtained using adult plants having mature leaves. For optimal yields of flower production, the plants should have a maximum number of young meristems. Serotonin can be used to delay the onset of floral buds until the desired number of young meristems are present. Serotonin is applied in the same manner as the melatonin derivatives.

The following examples are provided by way of illustration only and not by way of limitation. Those of skill will readily recognize a variety of noncritical parameters which could be changed or modified to yield essentially similar results.

EXAMPLES

EXAMPLE 1

Radioimmunoassays Establishing the Presence and Cyclical Increase of Melatonin in Plants Plant Material: Uniform and rapid germination of *Pharbitis nil* seeds was achieved by scarifying seeds in concentrated sulfuric acid for 45 minutes. Seeds were thoroughly rinsed and then soaked overnight in aerated distilled water. The next morning, imbibed and germinating seeds were selected and planted in trays (approximately 100 seeds/tray filled with vermiculite. Seedlings were grown in an growth chamber at 27° C., continuously illuminated by cool-white 215-W fluorescent bulbs (Sylvania) providing an average of 250 $\mu$E $m^{-2}s^{-1}$ at plant height and watered daily with alternating distilled water or 2.82g/gallon 20-10-20 fertilizer solution (Grow More, 15600 New Century Drive, Gardena, Calif. 90248-2140). On the evening of the fifth day after planting, trays of seedlings to be given dark treatments were moved to a dark chamber within a darkroom. The temperature was maintained at 25° C.

Approximately 20 cotyledons per timepoint were harvested in complete darkness directly into liquid nitrogen. Frozen, pulverized tissue was stored in lightproof containers in the dark at −80° C. until later use in extraction.

For melatonin extractions from tabacco, *Nicotiana Sylvestris L.*, Vars. Hicks and Slyvestris, the above methods were followed.

Extraction and Quantification: In order to make accurate determinations of melatonin, it was necessary to lyophilize the tissue after having finely ground it with mortar and pestle in liquid nitrogen. Our most effective extraction protocol is a modification of that described by Poggeler et al. (1991). An important aspect of this protocol is minimization of exposure of tissue and extracts to light; therefore, most steps were conducted in total darkness or under dim illuminated by a red safe light.

Briefly, lyophilate (around 0.02 g) was aliquoted into tared 2.0 mL microcentrifuge tubes, allowed to equilibrate to room temperature in vacuo, and weighed. The powder was mixed with 200 $\mu$L of ice-cold 1M tris-NaOH buffer, pH 7.8, and extracted with 900 $\mu$L of ice-cold acetone (Fisher) overnight at −20° C. Debris was pelleted at 14,000 rpm by microcentrifugation (Eppendorf 5415C) for ten minutes at 5° C. The pellet was washed once with 250 $\mu$L of acetone and the supernatant dried under vacuum with centrifugation. Residue was resuspended in 2.0 ml of assay buffer (Fraser, et al., 1983) and shaken overnight at 7° C. to redissolve. Buffer-insoluble particles were pelleted as before.

Melatonin in 500 $\mu$L of supernatant was measured by radioimmunoassay with anti-melatonin antiserum (G/S/704-8483) from Stockgrand, Ltd. (Guildford Surrey, United Kingdom) following standard procedures for this RIA (Fraser, et al.,1983, *Clinical Chem* 29: 396-397) in which endogenous melatonin is competed with excess 79 Ci/mmol [0-methyl-$^3$H-melatonin (Amersham International, United Kingdom) for antibody binding. Unbound label is removed with activated 100-400 mesh charcoal (Sigma) pretreated with dextran (Pharmacia, N.J.). Bound label was quantified by liquid scintillation counting (Beckman LS8000) of 0.5 mL of supernatant in 4.5 mL a toluene-based scintillation fluid (Fisher). Timepoints were assayed in triplicate, and melatonin content calculated from a standard curve made with melatonin standards in assay buffer. The quenching effect of pigments in plant extract was corrected using dual channel counting and a quench curve [Counting Efficiency (CE) versus Sample Channel Ratio] made from extracts spiked with a label of known DPM (disintegrations per minute) (Long EC, 1976, Liquid Scintillation Counting Theory and Techniques. Beckman, Fullerton, Calif.).

CE was calculated as follows: CE=cpm/dpm, and can be calculated from the equation for the quench curve. The DPM for each sample was calculated using the formula DPM=cpm/CE.

Figure 2:
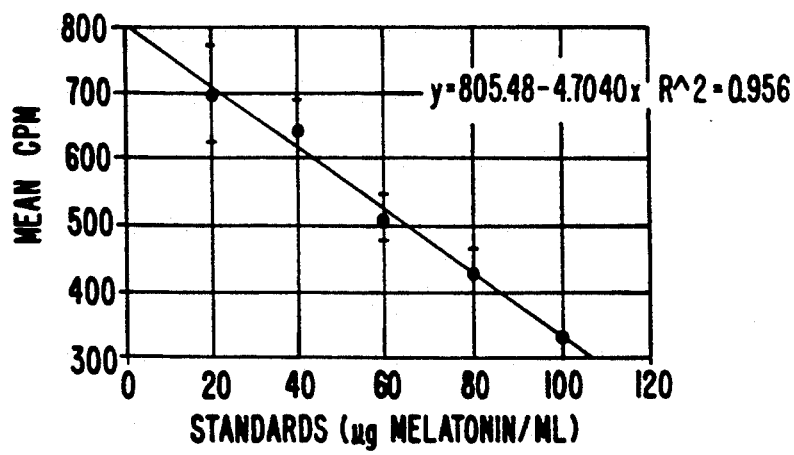
FIG. 2 is a standard curve for a melatonin radioimmunoassay.
Figure 3:
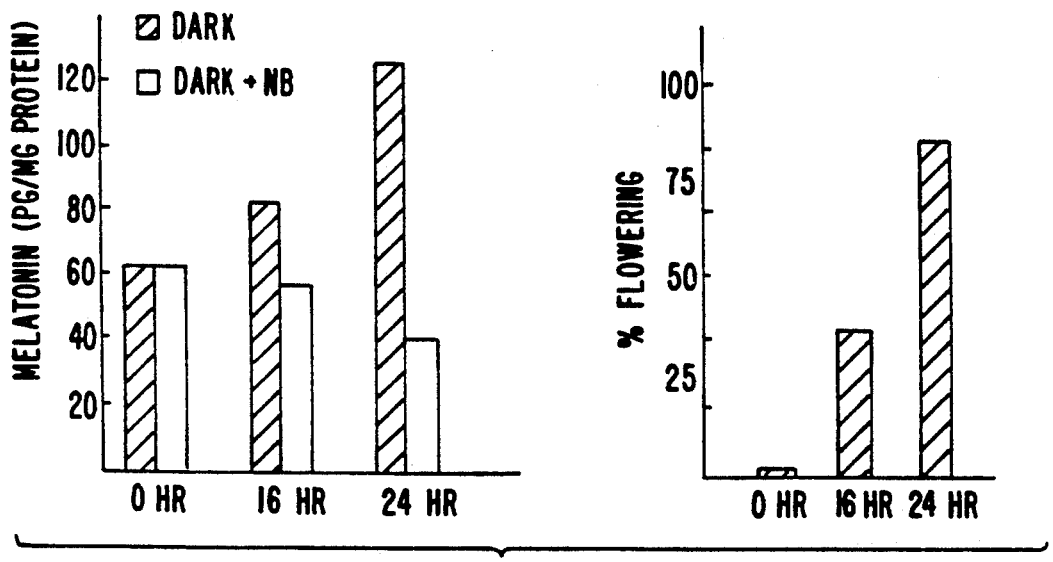
FIG. 3 provides melatonin content as determined by radioimmunoassays of pharbitis nil cotyledons after 0, 16 and 24 hours of darkness (dark) or with a 10 minute interruption of red light 8 hours into the dark period (Dark+NB) (left panel). The right panel shows the extent of flower induction at each time point that melatonin levels were determined. No flowering was observed in Dark+NB treated seedlings.
Figure 4:
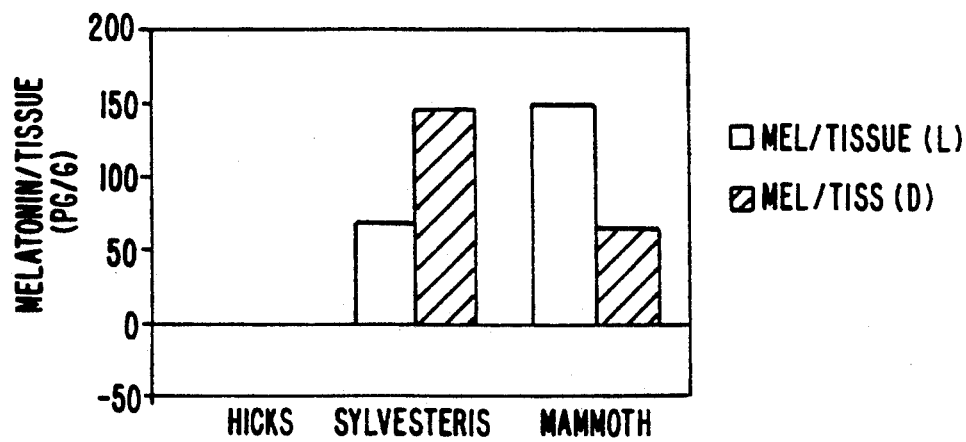
FIG. 4 provides the melatonin content of day-neutral (Hicks), long-day (Sylvestris) or short-day (Mammoth) tobacco sampled from plants at the midpoint of a 12 hour light (open bar) or 12 hour dark (hatched bar) period.

The results are provided in FIGS. 2-4. Clearly the proportion of melatonin is increasing with increased dark periods in short-day plants. The day-neutral and long-day tobacco do not respond to increased darkness by increasing melatonin levels.

EXAMPLE 2

This Example illustrates a composition according to the invention in the form of an emulsifiable concentrate formulation of melatonin suitable for dilution with water.

|  | % Weight/Volume |
|---|---|
| Melatonin | 20 |
| Condensate of 2 moles ethylene oxide with a mixture of oleyl and cetyl alcohols | 5 |
| Mixture of calcium dodecyl benzene sulphonate with ethoxylated castor oil | 5 |
| Technical grade methylcyclohexanone to 100% | |

EXAMPLE 3

This Examples illustrates a solid composition according to the invention comprising melatonin suitable for application in the form of granules.

|  | Weight % |
|---|---|
| Melatonin | 3 |
| Pumice granules | 97 |
|  | 100% |

EXAMPLE 4

This example illustrates the preparation of a dust:

6 parts of serotonin, 47 parts of talc and 47 parts of clay are blended in a mixer and then powdered with a hammermill to give a dust.

EXAMPLE 5

This example illustrates the preparation of a wettable powder:

25 parts melatonin, 54 parts of clay, 10 parts of diatomaceous earth, 5 parts of white carbon, 3 parts of sodium ligninsulphonate, 2 parts of Newcoal-1106 (a trade name for a surfactant of Nippon Nyukazai K. K., Japan) and 1 part of polyvinyl alcohol are blended homogeneously in a mixer and powdered three times in a hammermill to give a wettable powder.

EXAMPLE 6

Foliar Application of Melatonin on Plants

*Pharbitis nil* are grown until 5-7 shoot meristems are visible. The plants are then sprayed with a the formulation of example 2 diluted to 25 ppm melatonin.

EXAMPLE 7

As set forth in Example 6 but substituting 5 methoxytryptamine for melatonin.

EXAMPLE 8

As set forth in Example 6 but substituting N-acetyl serotonin for melatonin.

EXAMPLE 9

Foliar Application of Serotonin on Plants

*Pisum sativum* are grown for 35 days under optimal growing conditions. Two treatments of serotonin are applied at 15 and 17 days. The serotonin is prepared as a dust according to Example 4. When a suitable number of meristems are visible, the plants are then sprayed with a formulation of melatonin according to Example 6.

What is claimed is:

1. A method for regulating the flowering of a plant by applying a compound of the formula I in an amount sufficient to induce flowering $$\text{(I)}$$

wherein $R^1$ is selected from the group consisting of hydrogen and lower alkyl of 1 to 4 carbon atoms;

$R^2$ is selected from the group consisting of hydrogen and alkyl of 1 to 4 carbon atoms;

$R^3$ is selected from the group consisting of hydrogen and $-COR^4$ wherein $R^4$ is a alkyl of 1 to 4 carbon atoms; and $R^5$ and $R^6$ are independently selected from the group consisting of hydrogen, chloro, fluoro, bromo and iodo.

2. A method of claim 1 wherein $R^1$ is a methyl, $R^2$ is hydrogen, $R^3$ is hydrogen, $R^5$ is hydrogen, and $R^6$ is hydrogen.

3. A method of claim 1 wherein $R^1$ is a methyl or ethyl, $R^2$ is hydrogen, $R^3$ is $COR^4$ where $R^4$ is methyl, $R^5$ and $R^6$ are hydrogen.

4. A method of claim 1 wherein the compound is 5-methoxy N-acetyltryptamine.

5. A method of claim 1 wherein the compound is 5-methoxytryptamine.

6. A method of claim 1 wherein the plant is a monocot.

7. A method of claim 1 wherein the plant is a dicot.

8. A method of claim 1 wherein the plant is a photoperiodic plant.

9. A method of claim 1 wherein the plant is a short-day plant.

10. A method of claim 1 wherein the compound is applied to the foliage in an aqueous solution.

11. A method of claim 10 wherein the compound is applied at a concentration of 0.5 ppm to 1000 ppm.

12. A method of claim 10 wherein the compound is applied at a concentration of 10 ppm to 100 ppm.

13. A method of claim 10 wherein the compound is applied at a rate of 1 to 20 kg per hectare.

14. A method of claim 1 wherein the compound is applied after the plant has produced at least one fully expanded leaf.

15. A foliar formulation suitable for dilutation with water comprising a surfactant and a composition of the formula of claim 1 wherein the surfactant is selected from the group consisting of Tween ® 20 and Triton ® X-100.

16. A solution of claim 15 wherein the composition is 5-methoxy N-acetyltryptamine.

17. A method for regulating the flowering a plant by applying a compound selected from the group consisting of serotonin and N-acetylserotonin in an amount sufficient to control flowering.

18. A method of claim 17 wherein the compound is serotonin.

19. A method of claim 17 wherein the plant is a monocot.

20. A method of claim 17 wherein the plant is a dicot.

21. A method of claim 17 wherein the plant is a photoperiodic plant.

22. A method of claim 17 wherein the plant is a short-day plant.

23. A method of claim 17 wherein the compound is applied to the foliage in an aqueous solution.

24. A method of claim 23 wherein the compound is applied at a concentration of 0.5 ppm to 1000 ppm.

25. A method of claim 24 wherein the compound is applied at a concentration of 10 ppm to 100 ppm.

26. A method of claim 23 wherein the compound is applied at a rate of 1 to 20 kg per hectare.

27. A method of claim 17 wherein the compound is applied after the plant has produced at least one fully expanded leaf.

28. A foliar formulation suitable for dilution with water comprising a surfactant and a composition of the formula of claim 1 wherein the surfactant is selected from the group consisting of Triton® X-100 and Tween® 20.

* * * * *